United States Patent
Nakayama

(10) Patent No.: US 12,426,824 B2
(45) Date of Patent: Sep. 30, 2025

(54) EXAMINATION RESULT ESTIMATION DEVICE, PROGRAM, AND PROGRAM STORAGE MEDIUM

(71) Applicant: Medboost, Inc., Tokyo (JP)

(72) Inventor: Masafumi Nakayama, Tokyo (JP)

(73) Assignee: MEDBOOST, INC., Tokyo (JP)

( * ) Notice: Subject to any disclaimer, the term of this patent is extended or adjusted under 35 U.S.C. 154(b) by 0 days.

(21) Appl. No.: 18/022,072

(22) PCT Filed: Mar. 16, 2021

(86) PCT No.: PCT/JP2021/010688
§ 371 (c)(1),
(2) Date: Feb. 17, 2023

(87) PCT Pub. No.: WO2022/038819
PCT Pub. Date: Feb. 24, 2022

(65) Prior Publication Data
US 2023/0363688 A1    Nov. 16, 2023

(30) Foreign Application Priority Data
Aug. 21, 2020   (JP) .................. 2020-140479

(51) Int. Cl.
*A61B 5/05* (2021.01)
*A61B 5/00* (2006.01)
*A61B 5/346* (2021.01)
*A61B 8/08* (2006.01)
*G06T 1/00* (2006.01)
*G06T 7/00* (2017.01)

(52) U.S. Cl.
CPC ............ *A61B 5/346* (2021.01); *A61B 5/0044* (2013.01); *A61B 8/0883* (2013.01); *G06T 1/0007* (2013.01); *G06T 7/0014* (2013.01); *G06T 2207/10004* (2013.01); *G06T 2207/30048* (2013.01)

(58) Field of Classification Search
CPC ...... A61B 5/346; A61B 5/0044; A61B 8/0883
See application file for complete search history.

(56) References Cited

U.S. PATENT DOCUMENTS

2019/0183366 A1    6/2019   Dehghan Marvast et al.
2020/0205745 A1*   7/2020   Khosousi ............... G16H 50/20

FOREIGN PATENT DOCUMENTS

JP    2002-243706 A    8/2002
JP    2018-503885 A    2/2018
(Continued)

OTHER PUBLICATIONS

Official Communication issued in International Patent Application No. PCT/JP2021/010688, mailed on Jun. 22, 2021.
(Continued)

*Primary Examiner* — Joel F Brutus
(74) *Attorney, Agent, or Firm* — Keating & Bennett, LLP

(57) ABSTRACT

Provided is an examination result estimation device that includes: a signal acquisition unit that acquires an electrocardiogram signal; an estimation unit that estimates an echocardiography result corresponding to the electrocardiogram signal acquired by the signal acquisition unit, by using a learned model obtained by machine learning using an electrocardiogram signal for learning as input data, and an echocardiography result as teacher data; and an output unit that outputs the echocardiography result estimated by the estimation unit.

9 Claims, 7 Drawing Sheets

(56) References Cited

FOREIGN PATENT DOCUMENTS

| JP | 2019-514635 | A  | 6/2019  |
|----|-------------|----|---------|
| JP | 2020-520273 | A  | 7/2020  |
| WO | 2016/077786 | A1 | 5/2016  |
| WO | 2017/171637 | A1 | 10/2017 |
| WO | 2018/210714 | A1 | 11/2018 |
| WO | 2018/211687 | A1 | 11/2018 |
| WO | 2019070978  | A1 | 4/2019  |

OTHER PUBLICATIONS

Furubayashi et al., "A study on normal abnormal determination of electrocardiogram waveform using deep learning", USAI Technical Report, vol. 5, No. 5, Mar. 15, 2018, pp. 1-5.

Goto et al., "Artificial intelligence to predict needs for urgent revascularization from 12-leads electrocardiography in emergency patients", PLOS One, Jan. 9, 2019, pp. 1-10.

Izumi et al., "Guideline on the Management of Valvular Heart Disease", JCS/JATS/JSVS/JSCS 2020, Mar. 13, 2020, pp. 1-132.

"Ultrasound screening of Fetalheart using AI", Fujitsu Journal, Feb. 20, 2019, 7 pages.

Kagiyama et al., "Machine Learning Assessment of Left Ventricular Diastolic Function Based on Electro cardiographic Features", Journal of The American College of Cardiology, vol. 76, No. 8, Aug. 25, 2020, pp. 930-941.

Attia et al., "Screening for cardiac contractile dysfunction using an artificial intelligence-enabled electrocardiogram", Nature Medicine, vol. 25, Jan. 2019, 9 pages.

Kwon et al., "Deep Learning-Based Algorithm for Detecting Aortic Stenosis Using Electrocardiography", Journal of the American Heart Association, 2020, 16 pages.

\* cited by examiner

| Time(msec) | I | II | III | aVR | aVL | aVF | V1 | V2 | V3 | V4 | V5 | V6 |
|---|---|---|---|---|---|---|---|---|---|---|---|---|
| 0 | -0.059 | -0.083 | -0.024 | 0.07 | -0.017 | -0.053 | 0.151 | 0.043 | -0.201 | -0.307 | -0.209 | -0.156 |
| 2 | -0.063 | -0.083 | -0.019 | 0.073 | -0.021 | -0.051 | 0.151 | 0.048 | -0.195 | -0.307 | -0.209 | -0.151 |
| 4 | -0.073 | -0.093 | -0.019 | 0.082 | -0.026 | -0.056 | 0.151 | 0.048 | -0.201 | -0.307 | -0.209 | -0.146 |
| 6 | -0.073 | -0.102 | -0.029 | 0.087 | -0.021 | -0.065 | 0.156 | 0.048 | -0.201 | -0.312 | -0.214 | -0.151 |
| ... | ... | ... | ... | ... | ... | ... | ... | ... | ... | ... | ... | ... |

SL (Sa)

Report of echocardiography estimation result

Estimated value

```
AOD valsalva  ** mm    ascending Ao ** mm    abdominal Ao ** mm
LAD           ** mm    LAD-4CV-  **×**mm (**×**)
```

M-mode                              B-mode

```
RVD        ** mm              IVST       ** mm (**-**)
LVDd       ** mm (**-**)      PWT        ** mm (**-**)
LVDs       ** mm (**-**)      LVDd       ** mm (**-**)
LVEDV      ** ml (**-**)
LVESV      ** ml (**-**)
SV         ** ml (**-**)
EF(teichholz) ** % (**-**)
LV mass index ** g/m²         EF(Bp)     ** % (**-**)
```

Doppler

Left ventricular blood inflow   E/A     Right ventricular blood outflow ACl/ET 
    DcT    ** msec
    e*     ** cm/sec
    E/e*               ASD, PFO    VSD **

```
Mitral valve  MR  (**)
              MS  (—)                jet area ** cm²
              MVA ** cm² (2D)
                  ** cm² (PHT)
       Valve diameter ** mm    PHT ** msec
```

```
Aortic valve  AR  (**)                AR PHT ** msec
              AS  (—)
              AVA ** cm² (2D)
                  ** cm² (Continuous expression)  Vmax ** m/s
       Valve diameter ** mm                       PGmax ** mmHg
```

```
Tricuspid valve  TR (**)      jet area ** cm²
       Vmax  ** m/s
       PGmax ** mmHg RVP (Right ventricular systolic pressure) ** mmHg
```

Pulmonary valve  PR (**)

B-mode IVC (Inferior vena cava diameter)  mm Collapse 
    Pericardial effusion **

Wall movement
Left ventricle→There is a possibility of anterior wall movement abnormality
Right ventricle→No abnormality

Congenital heart disease

Ventricular septal defect→High possibility
Atrial septal defect→Low possibility

FIG.10

EXAMINATION RESULT ESTIMATION DEVICE, PROGRAM, AND PROGRAM STORAGE MEDIUM

TECHNICAL FIELD

The present invention relates to an examination result estimation device for estimating results of echocardiography, as well as a program and a program storage medium for the same.

BACKGROUND ART

Conventionally, an examination using an electrocardiogram has been known. An examination using an electrocardiogram is an examination in which electrical activities of the heart are detected by electrodes on a body surface, and is used for finding, and checking the progress of, any heart disease such as irregular pulses, ischemic heart disease, and cardiomyopathy. In addition, electrocardiography is not an invasive examination, but is an examination that can be performed easily and inexpensively at any place. For this reason, electrocardiography has been esteemed as a screening examination in the health examination. However, much experience is required for reading electrocardiograms, and even an experienced physician has difficulty in diagnosing (making definite diagnosis) all of heart diseases only with electrocardiogram.

To make definite diagnosis, then, minute examination by echocardiography is required. Here, "echocardiography" means an examination performed by applying ultrasonic waves to a structure inside a body and obtaining an image by utilizing bounced, reflected waves. With echocardiography, it is possible to find structural abnormalities of the heart, such as abnormalities in heart valves, congenital abnormalities (a hole between a ventricle and an atrium, etc.), and expansion of a heart wall, an atrium, or a ventricle, which are seen in patients suffering from high blood pressure, heart failure, disorders in heart muscle walls (cardiomyopathy), and the like. In addition, in echocardiography, it is possible to measure the amount of blood pumped out by the heart per one pulse. Echocardiography is one of examination methods often used in the diagnosis of heart diseases, since it is useful for perceiving a structural abnormality of the heart, the blood flow volume of the heart, and the like, and is non-invasive to an examinee, as is the case with the electrocardiogram.

Even when an echocardiography device is possessed, however, an experienced physician or engineer is needed for extracting an appropriate image. In a medical underserved area, any cardiologist is not allocated, or any engineer who can perform ultrasonography is not allocated in some cases, and therefore, even if an echocardiography device is prepared, there is possibility that people there cannot receive appropriate medical treatment.

From these circumstances, a system for automatically determining a disease based on electrocardiogram was started to be developed, and for example, researches using electrocardiogram and machine learning (deep learning) in combination have been started. Such researches are disclosed in, for example, the following documents: Japanese Unexamined Patent Application Publications Nos. 2019-514635 and 2018-503885; Senami Furubayashi, Takeshi Imai, Sanshiro Ishihara, Katsuhito Fujio, and Kazuhiko Ohe, "*A study on normal abnormal determination of electrocardiogram waveform using deep learning*", JSAI Technical Report published by the Japanese Society for Artificial Intelligence, Mar. 15, 2018, vol. 5, no. 5, pp. 1 to 5; and Goto S, Kimura M, Katsumata Y, Goto S, Kamatani T, Ichihara G, Ko S, Sasaki J, Fukuda K, Sano M., "*Artificial intelligence to predict needs for urgent revascularization from 12-leads electrocardiography in emergency patients*", PLoS One (U.S.), 2019, 14(1), e0210103.

SUMMARY OF INVENTION

Problem to be Solved by the Invention

Though researches using electrocardiograms (electrocardiogram signals) and machine learning in combination have been started as described above, conventional researches have been intended to estimate the presence/absence of a specific disease, and to determine (estimate) whether the specific disease, if present, is severe, based on medical technologies at the point of time when the learning was performed. Medical technologies, however, are changing on a daily basis so that better medical treatments can be provided, and evaluation criteria for determining a medical treatment method are changing on a daily basis. For example, even taking aortic stenosis alone as an example, the determination of a surgical indication has been made based on severity in a clinical scene before, but recently the determination of a surgical indication is not necessarily dependent only on severity in clinical scene (see, for example, "2020 Guideline on the Management of Valvular Heart Disease" by Chisato Izumi and 33 others (Joint Guideline of the Japanese Circulation Society (JCS)/the Japanese Association for Thoracic Surgery (JATS)/the Japanese Society for Vascular Surgery (JSVS)/the Japanese Society for Cardiovascular Surgery (JSCS), Mar. 13, 2013). Specifically, when the heart has a low ejection fraction (calculated by dividing the amount of blood the heart pumps out by the capacity of the left ventricle during diastole), it is unlikely that a pressure gradient would occur at the aortic valve. In this case, a surgical indication is made in some cases, even if a severe aortic stenosis is not observed. The use of the device based on the above-described researches, therefore, only allows physicians to know estimation results based on relatively old medical technologies, which raises a problem that there are difficulties in making definite diagnosis. In light of this, an examination result estimation device that is capable of estimating examination results while being capable of coping with changes in medical technologies, even when an echocardiography device is not used, is desired, and so are a program and a program storage medium for the same.

This disclosure is intended to solve the problem as described above, and it is an object of the present disclosure to provide an examination result estimation device that is capable of estimating examination results while being capable of coping with changes in medical technologies, even when an echocardiography device is not used, as well as a program and a program storage medium for the same.

Means to Solve the Problem

To achieve the above-described object, an examination result estimation device according to a first aspect disclosed as follows includes: a signal acquisition unit that acquires an electrocardiogram signal; an estimation unit that estimates an echocardiography result corresponding to the electrocardiogram signal acquired by the signal acquisition unit, by using a learned model obtained by machine learning using an electrocardiogram signal for learning as input data, and an echocardiography result as teacher data; and an output unit that outputs the echocardiography result estimated by the estimation unit.

A program according to a second aspect causes a computer to execute processing comprising: acquiring an electrocardiogram signal; estimating an echocardiography result corresponding to the electrocardiogram signal, by using a learned model obtained by machine learning using an electrocardiogram signal for learning as input data, and an echocardiography result as teacher data; and outputting the estimated echocardiography result.

A program storage medium according to a third aspect is a computer-readable program storage medium in which a program is stored, wherein the program causes a computer to execute processing comprising: acquiring an electrocardiogram signal; estimating an echocardiography result corresponding to the electrocardiogram signal, by using a learned model obtained by machine learning using an electrocardiogram signal for learning as input data, and an echocardiography result as teacher data; and outputting the estimated echocardiography result.

Effect of the Invention

With the configurations according to the first to third aspects, it is possible to provide a physician with echocardiography results, even in a case where an echocardiography device is used, or in an area without a specialized physician or expert who can handle an echocardiography device. By confirming echocardiography results, a physician can perceive any structural abnormality of the heart, the blood flow volume of the heart, and the like. For this reason, a physician can appropriately examine a patient based on the latest medical technologies and echocardiography results (a structural abnormality of the heart, the blood flow volume of the heart, and the like), unlike a case with a conventional device that outputs severity of a disease based on relatively old medical technologies at the time of the diagnosis. In other words, it is possible to provide an examination result estimation device that is capable of estimating examination results while being capable of coping with changes in medical technologies, even when an echocardiography device is not used, as well as a program and a program storage medium for the same.

Figure 4:
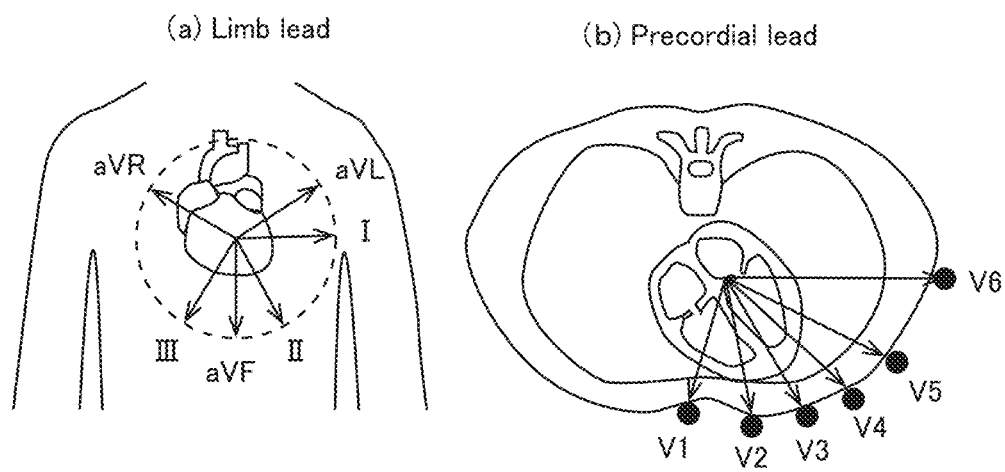

(a) of FIG. 4 explains limb lead in an electrocardiography in one embodiment. (b) of FIG. 4 explains precordial lead in electrocardiography in one embodiment.

Figure 5:
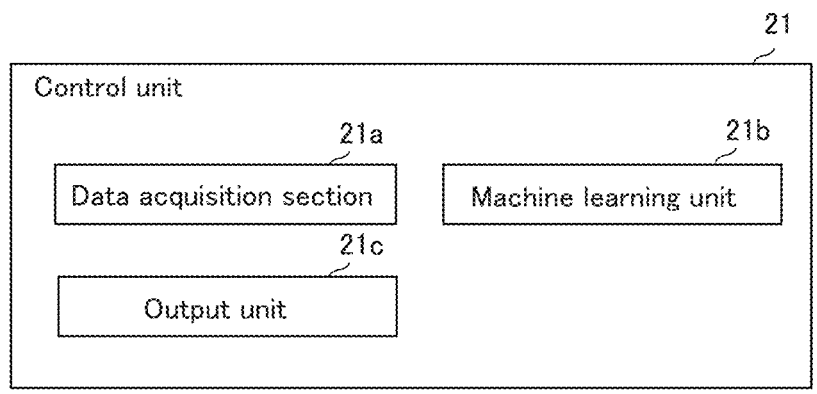

FIG. 5 is a functional block diagram of a control unit of a machine learning device in one embodiment.

Figures 6, 7:
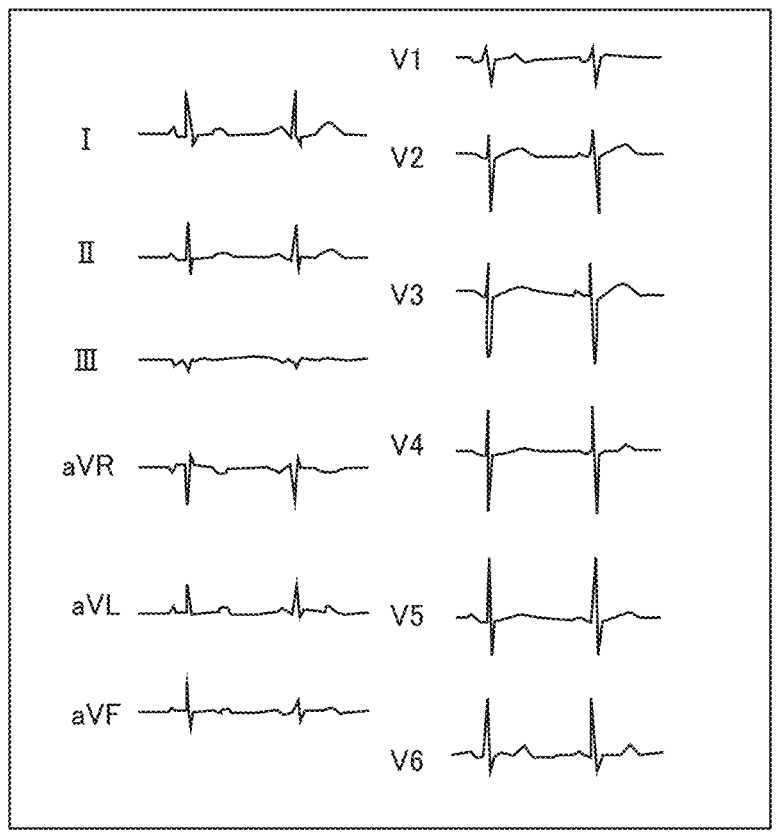

FIG. 6 explains exemplary waveforms of electrocardiogram signals in one embodiment.

FIG. 7 explains exemplary numerical data into which electrocardiogram signals are converted, in one embodiment.

Figure 8:
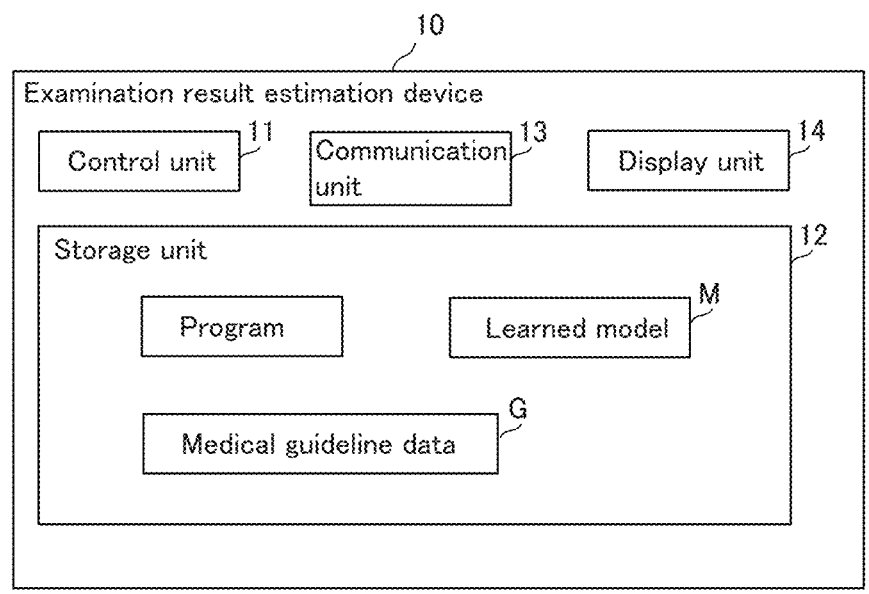

FIG. 8 is a block diagram illustrating a configuration of an examination result estimation device in one embodiment.

Figure 9:
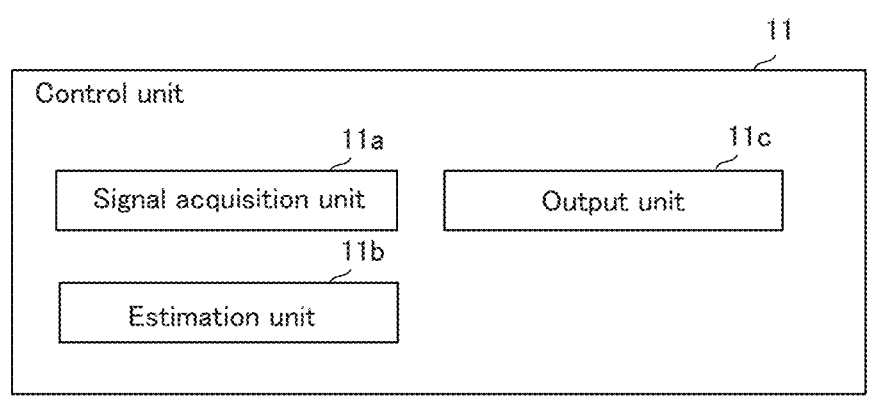

FIG. 9 is a functional block diagram of a control unit of an examination result estimation device in one embodiment.

FIG. 10 illustrates an exemplary screen showing echocardiography results (report) in one embodiment.

Figure 11:
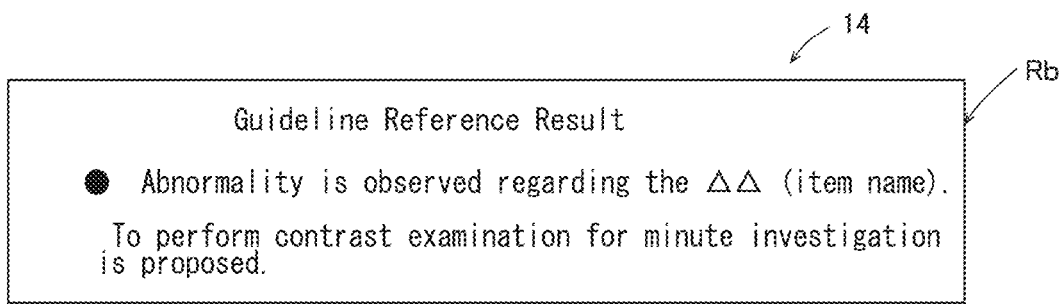

FIG. 11 illustrates an exemplary screen showing guideline reference results in one embodiment.

Figure 12:
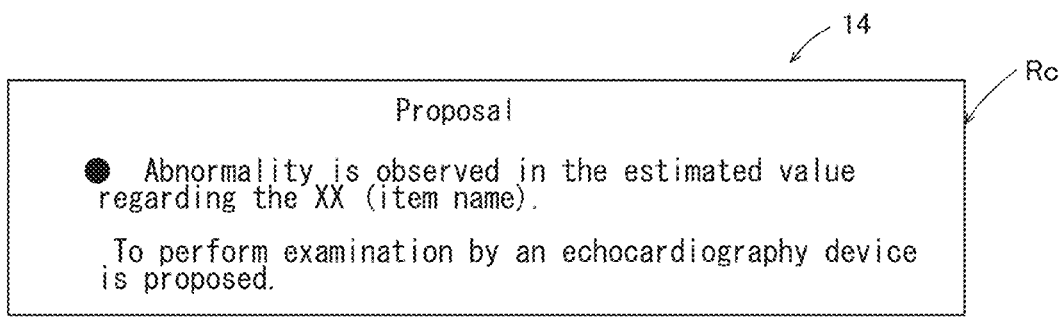

FIG. 12 illustrates an exemplary screen showing a proposal provided by an examination result estimation device in one embodiment.

Figure 13:
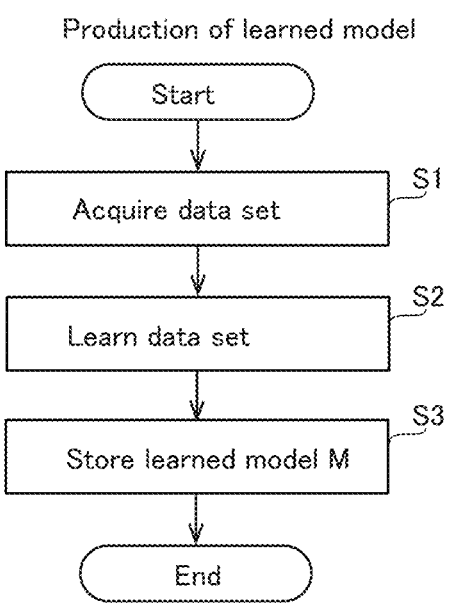

FIG. 13 is a flowchart for explaining a method for producing a learned model in one embodiment.

Figure 14:
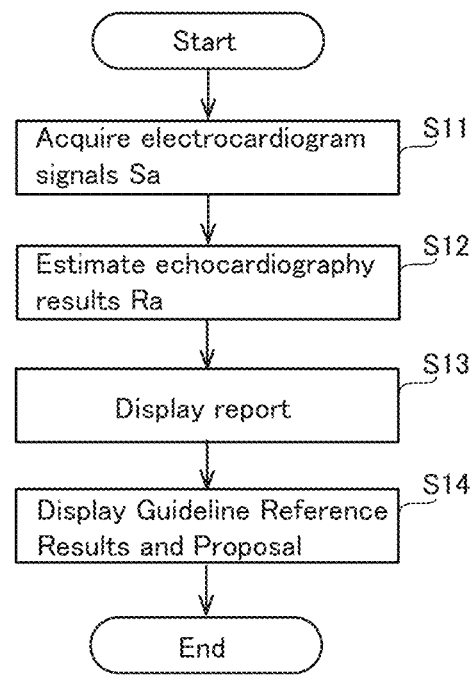

FIG. 14 is a flowchart for explaining a method for estimating echocardiography results in one embodiment.

MODE FOR CARRYING OUT THE INVENTION

One embodiment of the present invention is described below, based on the drawings. It should be noted that the present invention is not limited to the following embodiment, but the design can be appropriately varied in such a range that satisfies the configuration of the present invention. In addition, in the following descriptions, identical portions or portions having identical functions are denoted by the same reference symbols commonly in different drawings, and repeated descriptions of the same are omitted. The respective configurations described in the description of the embodiment and modification examples may be combined appropriately, and may be varied. To make the description easy to understand, in the drawings referred to hereinafter, the configurations are simply illustrated or schematically illustrated, or the illustration of part of constituent members is omitted,

[Overview of Examination Result Estimation System]

Figure 1:
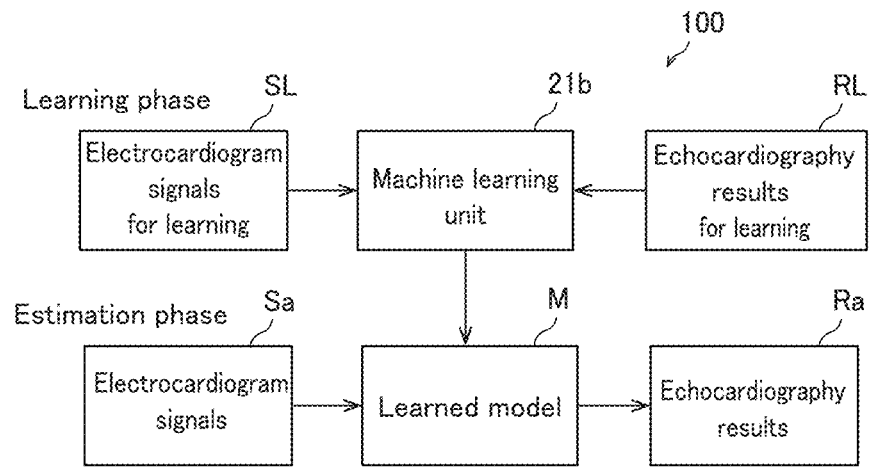
FIG. 1 explains an overview of a processing of an examination result estimation system in one embodiment.
Figure 2:
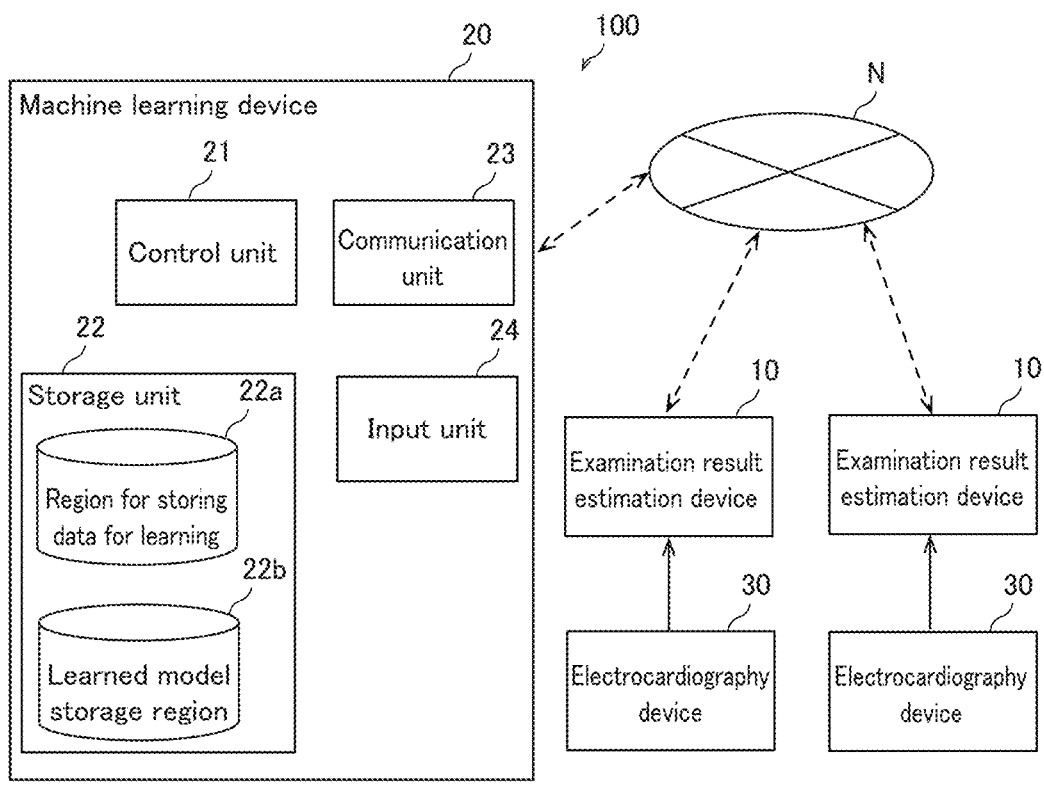
FIG. 2 is a block diagram illustrating an overall configuration of an examination result estimation system in one embodiment.

FIGS. 1 and 2 explain an overview of a configuration of an examination result estimation system 100 (hereinafter referred to simply as "the system 100") in the present embodiment. The system 100 is a system for estimating and outputting echocardiography results Ra outputting when electrocardiogram signals Sa are entered, for aiding a physician in making the diagnosis and treatment. Here, the "echocardiography results Ra" are equivalent to examination results obtained when echocardiography (echocardiogram examination) is performed, which contain, for example, information on the structure of the heart, the blood flow volume in the heart, and the like, which cannot be obtained only from the electrocardiogram signals Sa. Details of the echocardiography results Ra are to be described below with reference to FIG. 10.

As illustrated in FIG. 1, in the system 100, machine learning is performed by a machine learning unit 21b using data set including electrocardiogram signals SL for learning (hereinafter referred to as "learning electrocardiogram signals SL) as input data and echocardiography results RL for learning (hereinafter referred to as learning echocardiography results RL) as teacher data (learning phase), Here, the "learning electrocardiogram signals SL" are, for example, numerical data converted from electrocardiogram data prepared for performing the machine learning. The electrocardiogram data prepared for performing the machine learning may contain, for example, electrocardiogram data of a patient obtained by an electrocardiography device 30 (see FIG. 2), or may contain schematic electrocardiogram data produced by a machine or a human for learning. The electrocardiogram data prepared for performing the machine learning are not limited to unprocessed electrocardiogram data of a patient obtained by an electrocardiography device 30 (raw data), but may be data processed for learning. An example of the processing operation is described below.

The electrocardiogram data in the present embodiment are in accordance with, for example, Medical waveform Format Encoding Rules (MFER), or Digital Imaging and COmmunications in Medicine (DICOM). MFER is a standard obtained by normalization so that electrocardiograms, as well as all other medical waveforms such as, brain waveforms and breath waveforms, can be described, for the purpose of enabling easy conversion of waveforms into numerical values and images. For example, electrocardiogram data in accordance with MFER can be used in learning, storage, estimation, and display, as numerical data (CSV signals) obtained by Comma Separated Value (CSV) conversion in the system 100. In addition, DICOM is a standard that defines a communication protocol between medical imaging equipment, for the purpose of enabling image transfer between medical imaging equipment produced by different manufacturers. Incidentally, in the present disclosure, even electrocardiogram data in accordance with MFER or DICOM do not necessarily have to be CSV-converted, and for example, an MFER file or DICOM file may be used as an image in learning, storage, estimation, and display. In addition, electrocardiogram data are not limited to MFER and DICOM, and may be based on Joint Photographic Experts Group (JPEG) standard, as long as the data are image data.

As illustrated in FIG. 1, the system 100, using a learned model M produced by a machine learning unit 21b, estimates echocardiography results Ra corresponding to electrocardiogram signals Sa input thereto, and outputs the estimated echocardiography results Ra (estimation phase). Here, the "electrocardiogram signals Sa" are electrocardiogram data of a patient as an object of diagnosis, or data obtained by processing the electrocardiogram data or converting the data into numerical values. That is to say, the system 100 is configured to estimate echocardiography results Ra (echocardiogram examination results) of a patient as an object of this diagnosis based on electrocardiogram data of this patient. The electrocardiogram data referred in this paragraph are electrocardiogram data of a patient receiving medical examination in a medical facility that does not have an echocardiography device (for example, a clinic in a medical underserved area). Incidentally, details of the "learned model M are to be described below.

With this configuration, it is possible to provide a physician with echocardiography results Ra, even in a case where an echocardiography device is not available, or in an area without a physician or an expert who can handle an echocardiography device. By confirming echocardiography results Ra, a physician can perceive any structural abnormality of the heart, the blood flow volume of the heart, and the like. For this reason, a physician can appropriately examine a patient based on the latest medical technologies, a structural abnormality of the heart, the blood flow volume of the heart, and the like, unlike a case with a device that outputs severity of a disease based on relatively old medical technologies at the time of the diagnosis.

[Configuration of Each Portion of Examination Result Estimation System]

As illustrated in FIG. 2, the system 100 includes a plurality of examination result estimation devices 10 and a machine learning device 20. The machine learning device 20 is intended to execute the learning phase shown in FIG. 1. More specifically, the machine learning device 20 produces a learned model by performing machine learning by using a data set that includes learning electrocardiogram signals SL as input data and learning echocardiography results RL as teacher data. The examination result estimation device 10 is intended to execute the estimation phase shown in FIG. 1. More specifically, the examination result estimation device 10, using the learned model M, estimates echocardiography results Ra corresponding to electrocardiogram signals Sa input thereto, and outputs the estimated echocardiography results Ra.

The plurality of examination result estimation devices 10 and the machine learning device 20 are configured so as to communicate with each other via, for example, a network N. The plurality of examination result estimation devices 10 and the plurality of electrocardiography devices 30 are communicably connected, respectively. Incidentally, the network N is, for example, a local area network (LAN), a wide area network (WAN), the Internet, etc., but any other network may be used.

(Configuration of Electrocardiography Device)

Figure 3:
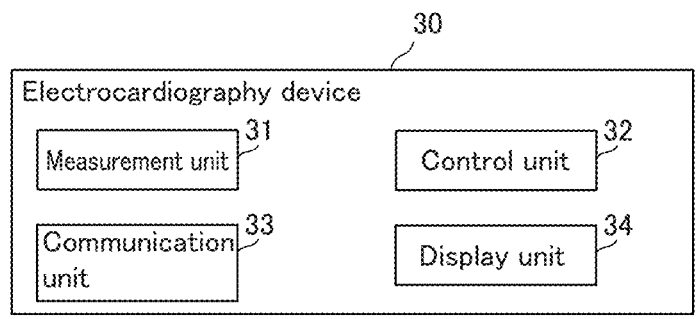
FIG. 3 is a block diagram illustrating a configuration of an electrocardiography device in one embodiment.

The electrocardiography device 30 is configured to perform electrocardiography by, for example, an examination method using a 12-lead electrocardiogram. As illustrated in FIGS. 3 and 4, the electrocardiography device 30 includes a measurement unit 31, a control unit 32, a communication unit 33, and a display unit 34. In the following description, the 12-lead electrocardiogram is to described by way of example, but in the present disclosure, the electrocardiogram signals Sa may be obtained by an examination method other than the examination method using the 12-lead electrocardiogram.

FIG. 4 is a diagram for explaining the examination method using the 12-lead electrocardiogram. As illustrated in FIG. 4, the 12 leads include six limb leads (I, II, III, aVR, aVL, and aVF) and six precordial leads (V1, V2, V3, V4, V5, and V6), and electric activity of the myocardium is represented by twelve vectors. The measurement unit 31 includes, for example, 12 measurement electrodes to be attached to 12 locations on a patient. The measurement unit 31 acquires 12 types of electrocardiogram signals Sa that represent 12-lead electrocardiogram data (see FIG. 6). The measurement unit 31 delivers the acquired electrocardiogram signals Sa to the control unit 32. The control unit 32 includes a processor. The control unit 32 displays the electrocardiogram signals Sa (waveforms) (see FIG. 6) on the display unit 34. In addition, the control unit 32 transmits the electrocardiogram signals Sa to the examination result estimation device 10 (see FIG. 2), via the communication unit 33, or by wired or wireless communication. In addition, the control unit 32 may transmit the learning electrocardiogram signals SL to the machine learning device 20, via the communication unit 33. The communication unit 33 is a communication interface. The display unit 34 is, for example, a liquid crystal display or an organic EL display.

The present embodiment is described by way of an example in which the display unit 34 is provided in the electrocardiography device 30, but a printing unit for printing the waveforms of the electrocardiogram signals Sa on a paper medium may be provided, in place of the display unit 34, or in addition to the display unit 34. In addition, as an example, the communication unit 33 is provided in the electrocardiography device 30, but a removable storage medium may be provided, in place of the communication unit 33, or in addition to the communication unit 33, in the electrocardiogram device 30. By using this storage medium, the electrocardiogram signals Sa may be transferred to the examination result estimation device 10, or the learning electrocardiogram signals SL may be transferred to the machine learning device 20, (Configuration of Machine Learning Device)

As illustrated in FIG. 2, the machine learning device 20 includes a control unit 21, a storage unit 22, a communication unit 23, and an input unit 24. The control unit 21 includes a processor that executes control processing by executing a program. The control unit 21 is configured to execute respective control processing operations of the machine learning device 20. The storage unit 22 includes a region 22a for storing data for learning (hereinafter referred to as "learning data storage region 22a) and a learned model storage region 22b. The communication unit 23 is a communication interface, and is connected to the network N. The input unit 24 may be a user interface such as a keyboard, a mouse, or a touch panel, or may be configured as an optical character recognizer (OCR) for reading a paper medium.

FIG. 5 is a functional block diagram of the control unit 21. The control unit 21 includes a data acquisition unit 21a, a machine learning unit 21b, and an output unit 21c. The data acquisition unit 21a acquires learning electrocardiogram signals SL from the electrocardiography device 30, or acquires learning electrocardiogram signals SL produced by a human or a machine. The data acquisition unit 21a stores the acquired learning electrocardiogram signals SL in the learning data storage region 22a, FIG. 6 is a diagram for explaining data (waveforms of electrocardiogram signals) of a 12-lead electrocardiogram. FIG. 7 is a diagram for explaining numerical data of the learning electrocardiogram signals SL (electrocardiogram signals Sa). The learning electrocardiogram signals SL are acquired as CSV-converted numerical data obtained by sampling the data of the 12-lead electrocardiogram (see FIG. 6) at predetermined timings. FIG. 7 schematically shows the CSV-converted numerical data in a table form. Incidentally, in the present disclosure, the learning electrocardiogram signals SL are not limited to CSV-converted numerical data, but waveform images of the 12-lead electrocardiogram may be used as the learning electrocardiogram signals SL The learning electrocardiogram signals SL may be signals (data) obtained by further processing the CSV-converted numerical data. For example, the control unit 21 may normalize heartbeat intervals of the learning electrocardiogram signals SL, "Normalization" means processing each signal in such a manner that the length per one heartbeat becomes uniform, so that the waveforms can be easily compared with one another. In addition, the control unit 21 may perform a processing operation of removing a linear portion (baseline) other than the PQRST waves, as well as noise components, from the learning electrocardiogram signals SL This eliminates factors such as heartbeat intervals and noises, in which individual differences tend to appear, thereby making it possible to improve accuracy in estimation of the learned model M to be produced. Incidentally, when the heartbeat interval is included as a characteristic point of the learning electrocardiogram signals SL, the learning electrocardiogram signal SL do not have to be normalized.

The data acquisition unit 21a acquires the learning echocardiography results RL. For example, electrocardiography and echocardiography are performed with respect to one same patient, and learning electrocardiogram signals SL and learning echocardiography results RL are acquired from these examinations by the data acquisition unit 21a. Here, the learning echocardiography results RL include at least one item out of the size of a portion of the heart, the blood flow volume in the heart, the blood flow velocity in the heart, and the blood pressure in the heart. More specifically, for example, the learning echocardiography results RL include structural dimensions of the heart including a left ventricle wall thickness, a left atrium dimension, and a valve port area, a blood flow volume such as a stroke volume, a pressure gradient that is necessary for the determination of the severity of a valvular disease, as well as a pressure in a ventricle, and other various items.

Further specifically, the learning echocardiography results RL include the following items; an aorta dimension (AOD); left atrium dimension (LAD); right venticular dimension (RVD); left ventricular end-diastolic dimension (LVDd); left ventricular end-systolic dimension (LVDs); left ventricular end-diastolic volume (LVEDV); left ventricular end-systolic volume (LVESV); stroke volume (SV); ejection fraction (EF); left ventricular mass index (LV mass index); interventricular septum thickness (IVST); posterior left ventricular wall thickness (PWT); information on left ventricular blood inflow (E/A, DcT, e', E/e'); information on right ventricular blood outflow (ACI/ET); mitral regurgitation (MR); mitral valve area (MVA); mitral valve diameter; pressure half time (PHT); aortic regurgitation (AR); aortic valve area (AVA); aortic valve diameter; tricuspid regurgitation (TR); jet area; right ventricular systolic pressure (RVP); pulmonary regurgitation (PR); inferior vena cava diameter (IVC); collapse; and pericardial effusion. In addition, the learning echocardiography results RL include information on cardiac wall movements, and information on congenital heart diseases. The information on cardiac wall movements includes, for example, information on which wall of the left ventricle or the right ventricle has abnormality. The information on congenital heart diseases includes information on the possibility of the presence of a ventricular septal defect or an atrial septal defect. The congenital heart diseases are not limited to the above-described two diseases, but may be another disease. The respective items of the learning echocardiography results RL are stored, for example, as numerical data in the learning data storage region 22a. In the present disclosure, the stored data are not limited to numerical data, but echocardiogram images may be stored as the learning echocardiography results RL in the learning data storage region 22a. Alternatively, the learning echocardiography results RL may be acquired by the data acquisition unit 21a, by input to the input unit 24, or by the reading of a paper medium by the input unit 24. The learning electrocardiogram signals SL and the learning echocardiography results RL are stored in the learning data storage region 22a, with correspondence to each other (as a data set).

As illustrated in FIG. 1, the machine learning unit 21E) has a function of producing a learned model M by performing, for example, learning-with-teacher. In other words, the machine learning unit 21b uses the learning electrocardiogram signals SL as input data, and learns the learning echocardiography results RL as teacher data (correct label) with respect to the input data (learning data). The machine learning unit 21b produces a learned model M by, for example, learning data sets of several hundred thousands of learning electrocardiogram signals SL and learning echocardiography results RL stored in the learning data storage region 22a. As a machine learning method used by the machine learning unit 21b, for example, deep learning with neural network can be used, but any other machine learning method other than deep learning may be used. When deep learning is used, the machine learning unit 21E) learns data sets, whereby parameters of functions in the neural network are optimized. The produced learned model M is stored in the learned model storage region 22b of the storage unit 22 (see FIG. 2).

The output unit 21c transmits the learned model M produced by the machine learning unit 21b via the communication unit 23 to each examination result estimation device 10. Each examination result estimation device 10 stores the received learned model M in its own storage unit 12 (see FIG. 8). Incidentally, an example in which the communication unit 23 is provided in the machine learning device 20 is described, but a removable storage medium may be provided, in place of the communication unit 23, or in addition to the communication unit 23, in the machine learning device 20. By using this storage medium, the learned model M may be transferred to the examination result estimation device 10.

The storage unit 22 is formed as, for example, a non-volatile memory. The storage unit 22 may be an on-premises-type (stationary) server. The storage unit 22, however, is not limited to an on-premises-type server, and a server on a cloud may be used.

[Configuration of Examination Result Estimation Device]

FIG. 8 is a block diagram illustrating a configuration of the examination result estimation device 10. The examination result estimation device 10 includes a control unit 11, a storage unit 12, a communication unit 13, and a display unit 14. The control unit 11 includes a processor that executes control processing by executing a program. The control unit 11 is configured to execute respective control processing operations of the examination result estimation device 10.

In the storage unit 12, programs for the control unit 11 to perform a processing operation, and the learned model M are stored. The storage unit 12 may be a storage device such as an on-premises-type (stationary) server. The storage device, however, is not limited to an on-premises-type server, and a storage device such as a server configured on a cloud so as to form the storage unit 12 may be used. In addition, the storage unit 12 may be removable from the examination result estimation device 10. In the storage unit 12, the learned model M produced by the machine learning device 20 may be stored preliminarily (at the time of manufacture of the examination result estimation device 10), or as described above, the learned model M may be received from the machine learning device 20 via the communication unit 13. Here, in the present embodiment, medical guideline data G are stored in the storage unit 12, In addition, the medical guideline data G include information on respective criteria for the items of the echocardiography results Ra, an examination method recommended in a case of an abnormal value (or abnormality) with respect to the criteria, and a treating method recommended in a case of an abnormal value (or abnormality) with respect to the criteria. The medical guideline data are, for example, criteria and procedures for diagnosis by a physician and determination of a treating method, prepared by medical academic societies (for example, the Japanese Circulation Society, the Japanese Association for Thoracic Surgery, the Japanese Society for Vascular Surgery, and the Japanese Society for Cardiovascular Surgery). Here, the medical guideline data G stored in the storage unit 12 are updated to the latest version as needed. The updating is performed by the control unit 11, As the medical guideline data G, for example, "Guideline on the Management of Valvular Heart Disease" can be used.

FIG. 9 shows a functional block diagram of the control unit 11. The control unit 11 includes a signal acquisition unit 11a, an estimation unit 11b, and an output unit 11c. The signal acquisition unit 11a is configured to acquire electrocardiogram signals Sa via the communication unit 13 from the electrocardiography device 30. More specifically, the signal acquisition unit 11a acquires electrocardiogram signals Sa that include numerical data (CSV signal) obtained by CSV-conversion from electrocardiogram image data (MFER or DICOM) of a patient as an object of medical examination. As numerical data have a smaller data size than electrocardiogram image data (MFER or DICOM), this configuration makes it possible to acquire electrocardiogram signals Sa more quickly from the electrocardiography device 30, and at the same time, to save the capacity of the storage unit 12. In addition, with the estimation unit 11b, processing load when echocardiography results Ra are estimated can be reduced.

FIG. 10 shows an exemplary report displayed on the display unit 14 (report of echocardiography estimation result). The estimation unit 11b, using the learned model M, performs a processing operation for estimating echocardiography results Ra corresponding to electrocardiogram signals Sa acquired. The output unit 11c outputs the estimated echocardiography results Ra to the display unit 14. More specifically, the output unit 11c outputs, to the display unit 14, a report in which a plurality of items included in the echocardiography results Ra are described. Regarding the echocardiography results Ra, the estimation unit 11b outputs estimated results as numerical data (CSV data) of the respective items of the following: structural dimensions of the heart including a left ventricle wall thickness, a left atrium dimension, and a valve port area; a blood flow volume such as a stroke volume; a blood flow velocity in the heart; a pressure gradient that is necessary for the determination of the severity of a valvular disease; as well as a pressure in a ventricle. More specifically, the estimation unit 11b outputs, for example, estimation results regarding the following items: an aorta dimension (AOD); left atrium dimension (LAD); right venticular dimension (RVD); left ventricular end-diastolic dimension (LVDd); left ventricular end-systolic dimension (LVDs); left ventricular end-diastolic volume (LVEDV); left ventricular end-systolic volume (LVESV); stroke volume (SV); ejection fraction (EF); left ventricular mass index (LV mass index); interventricular septum thickness (IVST); posterior left ventricular wall thickness (PWT); information on left ventricular blood inflow (E/A, DcT, e', E/e'); information on right ventricular blood outflow (ACI/ET); mitral regurgitation (MR); mitral valve area (MVA); mitral valve diameter; pressure half time (PHT); aortic regurgitation (AR); aortic valve area (AVA); aortic valve diameter; tricuspid regurgitation (TR); jet area; right ventricular systolic pressure (RVP); pulmonary regurgitation (PR); inferior vena cava diameter (IVC); collapse; and pericardial effusion. In addition, the estimation unit 11b outputs estimation results regarding cardiac wall movements and congenital heart diseases. The estimation results regarding cardiac wall movements include, for example, estimation results regarding which wall of the left ventricle or the right ventricle has abnormality. The estimation results regarding congenital heart diseases include estimation results regarding the possibility of the presence of a ventricular septal defect or an atrial septal defect. The estimation results regarding congenital heart diseases are not limited to the estimation results regarding the above-described two diseases, but may include those of another disease.

As illustrated in FIG. 10, the report describes patient information (patient ID, name, date of birth, sex, and age of a patient), examination day, department (for example, the cardiovascular department), name of doctor in charge, and the like. Further specifically, the report includes, for example, the following items: an aorta dimension (ADD); left atrium dimension (LAD); right venticular dimension (RVD); left ventricular end-diastolic dimension (LVDd); left ventricular end-systolic dimension (LVDs); left ventricular end-diastolic volume (LVEDV); left ventricular end-systolic volume (LVESV); stroke volume (SV); ejection fraction (EF); left ventricular mass index (LV mass index); interventricular septum thickness (IVST); posterior left ventricular wall thickness (PWT); information on left ventricular blood inflow (E/A, DcT, e E/e information on right ventricular blood outflow (ACI/ET); mitral regurgitation (MR); mitral valve area (MVA); mitral valve diameter; pressure half time (PHT); aortic regurgitation (AR); aortic valve area (AVA); aortic valve diameter; tricuspid regurgitation (TR); jet area; right ventricular systolic pressure (RVP); pulmonary regurgitation (PR); inferior vena cava diameter (IVC); collapse; and pericardial effusion. In addition, the report includes estimation results regarding cardiac wall movements and estimation results regarding congenital heart diseases. For example, as estimation results of cardiac wall movements, comments such as "there is a possibility of anterior wall movement abnormality" of the left ventricle", and "no abnormality" of the right ventricle are included. As the estimation results regarding congenital heart diseases, comments such as "high possibility" of a ventricular septal defect or "low possibility" of an atrial septal defect are included. The report may include information other than the above-described information (for example, estimation results regarding a disease other than the ventricular septal defect or the atrial septal defect). In addition, the examination result estimation device 10 may be provided with a printing function unit for printing a report on a paper medium.

A physician, viewing the report displayed on the display unit 14, can confirm the estimated echocardiography results Ra, even in a medical facility where an echocardiography device is not provided, Here, a physician can confirm information on the structure of the heart, the blood flow volume in the heart, and the like, which cannot be obtained only from the electrocardiogram signals Sa. As a result, the system 100 can aid a physician in making definite diagnosis for a patient, using the estimated information on the structure of the heart, the blood flow volume in the heart, and the like, FIG. 11 illustrates an exemplary screen showing guideline reference results displayed on the display unit 14. The estimation unit 11b outputs aid information Rb for aiding a physician in making diagnosis based on the echocardiography results Ra and the medical guideline data G. For example, the estimation unit 11b compares values of respective items of the echocardiography results Ra and reference values of the respective items included in the medical guideline data G. When any of the values of the items of the echocardiography results Ra is an abnormal value (or abnormality), the estimation unit 11b extracts an examination method for minutely investigating the presence or absence of a disease corresponding to the abnormal value (or abnormality) from the medical guideline data G, Then, the output unit 11c causes the display unit 14 to display the item having an abnormal value (or abnormality), and the examination method for minute investigation. For example, the output unit 11c causes the display unit 14 to display a message such as "Guideline Reference Result Abnormality is observed regarding the ΔΔ (item name), To perform contrast examination for minute investigation is proposed," Incidentally, the image shown in FIG. 11 may be displayed on the same screen where the image shown in FIG. 10 is displayed, or may be displayed on another screen.

FIG. 12 illustrates an exemplary screen showing a proposal (proposal to a physician) displayed on the display unit 14. When any of the items of the echocardiography results Ra was not estimated, or when the accuracy of an estimated value is low (an estimated range is greater a predetermined range), when an estimated value is a predetermined value (abnormal value), or the like, the estimation unit 11b produces a message of proposal displayed on the display unit 14. The output unit 11c causes the display unit 14 to display the message of the proposal. For example, the output unit 11c causes the display unit 14 to display a message such as "Abnormality is observed in the estimated value regarding the XX (item name). To perform examination by an echocardiography device is proposed." Incidentally, the image shown in FIG. 12 may be displayed on the same screen where the image shown in either one of FIGS. 10 and 11 is displayed, or may be displayed on another screen.

[Learned Model Producing Method]

Next, with reference to FIG. 13, a method for producing a learned model in the present embodiment is described. FIG. 13 is a flowchart relating to the production of a learned model. The processing operation relating to this producing method is executed by the control unit 21 of the machine learning device 20.

In Step S1, a data set of learning electrocardiogram signals SL and learning echocardiography results RL is acquired. For example, both of electrocardiography and echocardiography (echocardiogram examination) are performed with respect to one same patient. Then, using the electrocardiogram signals obtained by electrocardiography as the learning electrocardiogram signals SL, and using the information obtained by echocardiography as the learning echocardiography results RL, a data set of the learning electrocardiogram signals SL and the learning echocardiography results RL in correspondence with each other is produced. The data set is stored in the data storage unit 22. Incidentally, the learning electrocardiogram signals SL or the learning echocardiography results RL may be stored in a state of being processed (by normalization, noise processing, etc.) in the storage unit 22.

In Step S2, a plurality of data sets is learned. For example, a plurality (for example, several tens of thousands) of data sets are read out of the storage unit 22, and deep-learned, whereby a learned model M is produced. In step S3, the produced learned model M is stored in the storage unit 22.

[Method for Estimating Echocardiography Results]

Next, with reference to FIG. 14, a method for estimating echocardiography results Ra in the present embodiment is described. FIG. 14 is a flowchart relating to the estimation of echocardiography results Ra. The processing operation relating to this estimating method is executed by the control unit 11 of the examination result estimation device 10.

In Step S11, electrocardiogram signals Sa are acquired. These electrocardiogram signals Sa are obtained by electrocardiography performed with respect to a patient as an object of diagnosis.

In Step S12, using the learned model M, echocardiography results Ra corresponding to electrocardiogram signals Sa are estimated.

In Step S13, a report in which a plurality of items included in the estimated echocardiography results Ra are described (see FIG. 10) is displayed on the display unit 14. In Step S14, at least either one of Guideline Reference Results (see FIG. 11) and Proposal (see FIG. 12) is displayed. With this configuration, a physician can confirm echocardiography results Ra, even in a case where an echocardiography device is not available, or in an area without a physician or an expert who can handle an echocardiography device. By confirming echocardiography results Ra, a physician can perceive any structural abnormality of the heart, the blood flow volume of the heart, and the like. For this reason, a physician can appropriately examine a patient based on the latest medical technologies, a structural abnormality of the heart, the blood flow volume of the heart, and the like, unlike a case with a device that outputs severity of a disease based on relatively old medical technologies at the time of the diagnosis.

For example, in daily medical examination, a physician considers, based on echocardiography results Ra, whether another examination should be performed regarding the presence/absence of cardiac infarction, the severity of valvular disease, and the like. In addition, a physician suggests a suspected disease, and proposes an examination to be done next, based on the estimated echocardiography results Ra. This is performed not exclusively regarding heart diseases, but a physician makes a proposal regarding a disease other than heart diseases, if it is a disease such as pulmonary capillary embolism, pulmonary hypertension, or the like that can be presumed from the echocardiography results Ra.

Modification Examples

The above-described embodiments are merely examples for implementing the present invention. The present invention, therefore, is not limited to the above-described embodiment, and the above-described embodiment can be appropriately varied and implemented without departing from the spirit and scope of the invention.

(1) The foregoing embodiment is described with reference to an exemplary case in which the machine learning device, the examination result estimation device, and the electrocardiography device are configured as separate devices, but the present disclosure is not limited to this. In other words, two of the machine learning device, the examination result estimation device, and the electrocardiography device may be formed integrally.

(2) The foregoing embodiment is described with reference to an exemplary case in which estimated echocardiography results are displayed as a report including numerical data, but the present disclosure is not limited to this. For example, the estimated echocardiography results may be displayed as images (echocardiogram images).

(3) The foregoing embodiment is described with reference to an exemplary case in which electrocardiogram signals converted into numerical data are used in learning and estimation, but the present disclosure is not limited to this. For example, electrocardiogram image data may be used in at least either of learning and estimation.

(4) The foregoing embodiment is described with reference to exemplary items to be described in a report as shown in FIG. 10, but the present disclosure is not limited to this. In other words, only some of the items shown in FIG. 10 may be described, or items other than those shown in FIG. 10 may be included in the report.

(5) The foregoing embodiment is described with reference to an exemplary aspect in which a program for controlling operations of the control unit 11 of the examination result estimation device 10 is stored in the storage unit 12 such as a server. However, an arbitrary computer-readable storage medium (program storage medium) storing a program for controlling operations of a result estimation device, and a program transmitted wirelessly or via a communication line (program product) are also encompassed by the embodiment.

The above-described examination result estimation device, as well as a program and a program storage medium can be also described as follows:

An examination result estimation device according to a first configuration includes: a learned model obtained by machine learning using an electrocardiogram signal for learning as input data, and a echocardiography result for learning as teacher data; a signal acquisition unit that acquires an electrocardiogram signal; an estimation unit that, using the learned model, estimates an echocardiography result corresponding to the electrocardiogram signal acquired by the signal acquisition unit; and an output unit that outputs the echocardiography result estimated by the estimation unit (the first configuration).

With the first configuration, an estimated echocardiography result can be output, even in a medical facility where an echocardiography device is not provided. A physician, therefore, can confirm the estimated echocardiography result, thereby confirming information on the structure of the heart, the blood flow volume in the heart, and the like, which cannot be obtained only from the electrocardiogram signal. As a result, an examination result estimation device can be provided that can aid a physician in making definite diagnosis for a patient, using the estimated information on the structure of the heart, the blood flow volume in the heart, and the like.

In the first configuration, at least one item out of the size of a portion of the heart, the blood flow volume in the heart, the blood flow velocity in the heart, and the blood pressure in the heart may be included in the echocardiography result (the second configuration).

The second configuration allows a physician to recognize an estimation result of at least one item out of the size of a portion of the heart, the blood flow volume in the heart, the blood flow velocity in the heart, and the blood pressure in the heart, without using an echocardiography device.

In the first or second configuration, the output unit may be configured to display, on a display unit, a report in which a plurality of items included in the echocardiography result are described (the third configuration).

The third configuration allows a physician to confirm the echocardiography result easily, by viewing the report displayed on the display unit.

In any one of the first to third configurations, the signal acquisition unit may be configured to acquire an electrocardiogram signal that includes numerical data obtained by conversion from electrocardiogram image data (the fourth configuration).

The fourth configuration, which allows numerical data having a smaller data amount than electrocardiogram image data to be used, makes it possible to reduce processing load on the examination result estimation device.

In any one of the first to fourth configurations, the output unit may be configured to output an echocardiography result including numerical data (the fifth configuration).

The fifth configuration allows a physician to confirm numerical data, and thereby to confirm the echocardiography result easily, as compared with a case where an image itself of echocardiography is output.

In any one of the first to fifth configurations, the estimation unit may be configured to, using the learned model, estimate an echocardiography result corresponding to the electrocardiogram signal acquired by the signal acquisition unit, the echocardiography result including at least either of the presence/absence of wall movement abnormality and the presence/absence of a congenital heart disease (the sixth configuration).

The sixth configuration allows a physician to confirm an estimation result regarding at least either of the presence/absence of wall movement abnormality and the presence/absence of a congenital heart disease. The configuration, therefore, can aid a physician in making diagnosis and determining a treating method regarding wall movement abnormality or a congenital heart disease.

Any one of the first to sixth configurations may further include a storage unit in which medical guideline information is stored, wherein the estimation unit may be configured to generate aid information for aiding a physician in making diagnosis based on the estimated echocardiography result and the medical guideline information, and the output unit may be configured to output the echocardiography result estimated by the estimation unit and the aid information (the seventh configuration).

According to the seventh configuration, aid information based on not only the echocardiography result but also the medical guideline information is output. Therefore, when a physician refers to the aid information, the configuration can still further aid the physician in making diagnosis and determining a treating method.

A program according to the eighth configuration causes a computer to execute processing comprising: acquiring an electrocardiogram signal; estimating an echocardiography result corresponding to the acquired electrocardiogram signal, by using a learned model obtained by machine learning using an electrocardiogram signal for learning as input data, and an echocardiography result as teacher data; and outputting the estimated echocardiography result (the eighth configuration).

With the eighth configuration, it is possible to provide a program that enables to provide a physician with an echocardiography result that is necessary when the physician makes definite diagnosis, even in a case where an echocardiography device is not used, as is the case with the first configuration.

A program storage medium according to the ninth configuration is a computer-readable program storage medium in which a program is stored, wherein the program causes a computer to execute processing comprising: acquiring an electrocardiogram signal; estimating an echocardiography result corresponding to the acquired electrocardiogram signal, by using a learned model obtained by machine learning using an electrocardiogram signal for learning as input data, and an echocardiography result as teacher data; and outputting the estimated echocardiography result (the ninth configuration).

With the ninth configuration, it is possible to provide a program storage medium in which a program is stored that enables to provide a physician with an echocardiography result that is necessary when the physician makes definite diagnosis, even in a case where an echocardiography device is not used, as is the case with the first configuration.

DESCRIPTION OF REFERENCE NUMERALS

10; examination result estimation device
11a: signal acquisition unit
11b: estimation unit
11c: output unit
12: storage unit
14: display unit
M: learned model
RL: echocardiography result for learning (learning echocardiography result)
Ra: echocardiography result
Rb: aid information
SL: electrocardiogram signal for learning (learning electrocardiogram signal)
Sa: electrocardiogram signal

The invention claimed is:

1. An examination result estimation device comprising:
a processor; and
a storage to store medical guideline information including at least one of an examination method recommended in a case of an abnormal echocardiography result or a treating method recommended in a case of an abnormal echocardiography result, and prepared by medical academic societies; wherein
the processor is configured or programmed to:
acquire an electrocardiogram signal;
estimate an echocardiography result corresponding to the electrocardiogram signal, by using a learned model obtained by machine learning using electrocardiogram signals and echocardiography results including echocardiography numerical data extracted from results of echocardiography examinations performed on subjects and not including echocardiogram images of the results of echocardiography examinations;
generate aid information to aid a physician in making diagnosis based on the echocardiography result and the medical guideline information;
output the echocardiography result; and
output, when the echocardiography result is abnormal, aid information including at least one of the examination method or the treating method.

2. The examination result estimation device according to claim 1,
wherein the echocardiography result for learning includes at least one item out of a size of a portion of a heart, a blood flow volume in the heart, a blood flow velocity in the heart, and a blood pressure in the heart.

3. The examination result estimation device according to claim 1,
wherein the processor is configured or programmed to display, on a display, a report in which a plurality of items included in the echocardiography result is described.

4. The examination result estimation device according to claim 1,
wherein the processor is configured or programmed to acquire an electrocardiogram signal that includes numerical data obtained by conversion from electrocardiogram image data.

5. The examination result estimation device according to claim 4,
wherein the processor is configured or programmed to output the echocardiography result including the numerical data.

6. The examination result estimation device according to claim 1,
wherein the processor is configured or programmed to, using the learned model, estimate the echocardiography result corresponding to the electrocardiogram signal, the echocardiography result including at least either of the presence/absence of wall movement abnormality and the presence/absence of a congenital heart disease.

7. A computer-readable program storage medium in which a program is stored,
wherein the program causes a computer to execute processing comprising:
storing medical guideline information including at least one of an examination method recommended in a case of an abnormal echocardiography result or a treating method recommended in a case of an abnormal echocardiography result, and prepared by medical academic societies;

acquiring an electrocardiogram signal;

estimating an echocardiography result corresponding to the electrocardiogram signal, by using a learned model obtained by machine learning using electrocardiogram signals and echocardiography results including echocardiography numerical data extracted from results of echocardiography examinations performed on subjects and not including echocardiogram images of the results of echocardiography examinations;

generating aid information to aid a physician in making diagnosis based on the echocardiography result and the medical guideline information;

outputting the echocardiography result; and outputting, when the echocardiography result is abnormal, the aid information including at least one of the examination method or the treating method.

8. An examination result estimation device comprising:

a processor; and a storage to store medical guideline information including at least one of an examination method recommended in a case of an abnormal echocardiography result or a treating method recommended in a case of an abnormal echocardiography result, and prepared by medical academic societies; wherein the processor is configured or programmed to:

acquire an electrocardiogram signal;

estimate an echocardiography result corresponding to the electrocardiogram signal, by using a learned model obtained by machine learning using an electrocardiogram signal for learning as input data, and an echocardiography result as teacher data;

generate aid information to aid a physician in making diagnosis based on the echocardiography result and the medical guideline information; and output the echocardiography result; and output, when the echocardiography result is abnormal, the aid information including at least one of the examination method or the treating method.

9. An examination result estimation device comprising:

a processor; and a storage; wherein the processor is configured or programmed to:

acquire an electrocardiogram signal;

estimate an echocardiography result corresponding to the electrocardiogram signal, by using a learned model obtained by machine learning using learning electrocardiogram signals, and learning echocardiography results including echocardiography numerical data extracted from results of echocardiography examinations performed on subjects and not including echocardiogram images of the results of echocardiography examinations; and output the echocardiography result.

* * * * *